United States Patent
Mochizuki (10) Patent No.: US 7,910,366 B2
(45) Date of Patent: Mar. 22, 2011

(54) CELL STRAIN CAPABLE OF BEING CULTURED WITHOUT INGREDIENTS DERIVED FROM ANIMALS, METHOD OF PRODUCING THE SAME, METHOD OF PRODUCING VIRUS USING THE SAME, AND METHOD OF PRODUCING VACCINE

(75) Inventor: Masami Mochizuki, Yokohama (JP)

(73) Assignee: Kyoritsu Seiyaku Corporation, Tokyo (JP)

( * ) Notice: Subject to any disclaimer, the term of this patent is extended or adjusted under 35 U.S.C. 154(b) by 671 days.

(21) Appl. No.: 11/885,833

(22) PCT Filed: Mar. 10, 2005

(86) PCT No.: PCT/JP2005/004240
§ 371 (c)(1),
(2), (4) Date: Sep. 7, 2007

(87) PCT Pub. No.: WO2006/095431
PCT Pub. Date: Sep. 14, 2006

(65) Prior Publication Data
US 2008/0138362 A1    Jun. 12, 2008

(51) Int. Cl.
*C12N 15/85* (2006.01)
*C12N 7/00* (2006.01)

(52) U.S. Cl. .................................. 435/325; 435/235.1

(58) Field of Classification Search .................. None
See application file for complete search history.

(56) References Cited

U.S. PATENT DOCUMENTS

| 6,406,909 B1 | 6/2002 | Shibuya et al. |
| 2003/0044962 A1 | 3/2003 | Makizumi et al. |
| 2004/0077086 A1 | 4/2004 | Reiter et al. |

FOREIGN PATENT DOCUMENTS

| EP | 1 096 017 A2 | 5/2001 |
| WO | WO-00/03000 | 1/2000 |
| WO | WO-01/23527 A1 | 4/2001 |
| WO | 2004/005493 A1 | 1/2004 |
| WO | WO-2004/078955 A1 | 9/2004 |
| WO | WO-2004/110484 A1 | 12/2004 |

OTHER PUBLICATIONS

XP-009110058: Gut, J., et al.,"Cryptosporidium parvum: In Vitro Cultivation in Madin-Darby Canine Kidney Cells", *The Journal of Protozoology*, vol. 38, No. 6, pp. 72S-73S, (Nov. 11, 1991).

XP-005294671: Mochizuki, M. , "Growth characteristics of canine pathogenic viruses in MDCK cells cultured in RPMI 1640 medium without animal protein" *Vaccine* Butterworth Scientific Guildford, GB, vol. 24, No. 11, pp. 1744-1748, (Mar. 10, 2006).

XP-000982880: Merten, O. W. et al., "Production of Influenza Virus in Cell Cultures for Vaccine Preparation", *Advances in Experimental Medicine and Biology* Spring St., NY, vol. 397, pp. 141-151, (Jan. 1, 2006).

Merten, O.W., et al.,"The new medium MDSS2N free of any animal protein supports cell growth and production of varius viruses", *Cytotechnology*, vol. 30, No. 1/3, pp. 191-201, (1999).

Kagaku to Seibutsu, "Baiyo Dobutsu Saibokabu no Junka", vol. 29, No. 7, pp. 444-445, (1991).

Gekkan the Tissue Culture, "Tokushi Kabu Saibo no Tanjun Kankyo eno Junka, Mukessho Baichi Oyobi Glutamine Fugan Baichi eno Namaruba Saibo no Junka", vol. 18, No. 1, pp. 18-23, ( 1992).

Gekkan the Tissue Culture, "Nonaminal Bio Nutritional no Genjo", vol. 27, No. 13, pp. 528-531, (2001).

Merten, O.W., et al.,"A Simple Serum-free Freezing Medium for Serum-free Cultured Cells", *Biologicals*, vol. 23, pp. 185-189, ( 1995).

Makoschey, B. et al.,"Serum-free produced Bovine Herpesvirus type 1 and Bovine Parainfluenza type 3 virus vaccines are efficacious and safe", *Cytotechnology*, vol. 39, pp. 139-145, (2002).

Kessler, N., et al.,"Suitability of MDCK Cells Grown in a Serum-Free Medium for Influenza Virus Production", *Dev. Biol. Basel Karger*, vol. 98, pp. 13-21, (1999).

Merten, O.-W., et al. "Production of Influenza Virus in Serum-Free Mammalian Cell Cultures",*Dev. Biol. Stand. Basel. Karger*, vol. 98, pp. 23-37, (1999).

Voeten, J.T.M., et al. "Generation and Characterization of Reassortant Influenza a Viruses Propagated in Serum-Free Cultured MDCK-SF1 Cells," *Dev. Biol Stand, Basel Karger*, vol. 98, pp. 77-87, (1999).

Voeten, J.T.M., et al.,"Characterization of high-growth reassortant influenza a viruses generated in MDCK cells cultured in serum-free medium", *Vaccine*, vol. 17, pp. 1942-1950, (1999).

Froud, S.J., et al.,"The Development, Benefits and Disadvantage of Serum-Free Media", *Dev.Biol.Stand, Basel, Karger*vol. 99, pp. 157-166, (1999).

Merten, O.-W, "Safety Issues of Animal Products Used in Serum-Free Media," *Dev. Biol Stand. Basel, Karger*, vol. 99, pp. 167-180, (1999).

Merten, O.-W, Development of Serum-Free Media for Cell Growth and Production of Viruses/Viral Vaccines-Safety Issues of Animal Products Used in Serum-Free Media , *Dev. Biol. Basel Karger*, vol. 111, pp. 233-257, (2002).

Noe, W., et al.,"Fed-batch Strategies for Mammalian Cell Cultures", *Oxford, Butterworth-Heinemann*, pp. 413-418, (1994).

(Continued)

*Primary Examiner* — Zachariah Lucas
*Assistant Examiner* — Michelle Horning
(74) *Attorney, Agent, or Firm* — The Nath Law Group (57) ABSTRACT

The invention relates to a cell strain induced from MDCK cells as dog kidney-derived cells, and being able to be cultured without ingredients derived from animals. The cell strain is produced by adapting a MDCK cell to a medium without a serum but with a cell growth factor; and culturing the cell in a medium with an RPMI 1640 medium and a soybean-derived peptone but without ingredients derived from animals.

6 Claims, 7 Drawing Sheets

OTHER PUBLICATIONS

Merten, O._W, et al.,"A Simple Serum-free Freezing Medium for Serum-free Cultured Cells", *Biologicals*, vol. 23, pp. 185-189, (1995).

Merten, O.-W., et al.,"Evaluation of the new serum-free medium (MDSS2) for the production of different biologicals: Use of various cell lines", *Cytotechnology*, vol. 14, pp. 47-59, (1994).

Price, P.J., et al.,"Serum Free Medium without animal Components for Virus Production", *Focus*, vol. 19, No. 3, pp. 67-69, (1997).

Seki, F., et al., "Efficient Isolation of Wild Strains of Canine Distemper Virus in Vero Cells Expressing Canine SLAM(CD150)and their Adaptability to Marmoset B95a Cells", *Journal of Virology*, pp. 9943-9950, (Sep. 2003).

Official Action issued on Nov. 24, 2010, in counterpart Japanese application, three (3) pages.

CELL STRAIN CAPABLE OF BEING CULTURED WITHOUT INGREDIENTS DERIVED FROM ANIMALS, METHOD OF PRODUCING THE SAME, METHOD OF PRODUCING VIRUS USING THE SAME, AND METHOD OF PRODUCING VACCINE

TECHNICAL FIELD

The present invention relates to a cell strain capable of being cultured without ingredients derived from animals and a method of producing the same. In addition, the present invention also relates to a method of producing a virus using the above cell strain, a method of producing a diagnostic antigen, and a method of producing a vaccine. Moreover, the present invention also relates to a medium used for the culture of the above cell strain. Furthermore, the present invention also relates to a medium used for cryopreservation of the above cell strain and a cryopreservation method.

BACKGROUND ART

A half-century or more has passed since the creation of a technique of culturing animal cells and the like in a test tube. Such a technique has been significantly developed together with progression of science and technology.

In general, when a living animal is directly used for experiments, the results can be easily understood. However, such direct examination of a living animal has been problematic both technically and economically. Thus, a portion has been excised from an animal, and the cells thereof have been replicated in an artificial environment such as in a Petri dish or in a test tube. This method is called a tissue culture method or a cell culture method. Since such a technique has not been difficult, it has become possible to produce pharmaceuticals, vaccines, diagnostic antigens, etc., by this method. However, in order to culture animal cells in vitro, it is required to culture the cells almost under the same conditions as the original in vivo conditions. For example, conditions, such as an aseptic state or a temperature environment that is set at the same temperature as that in a living body, are applied.

Moreover, even if the aforementioned conditions have been satisfied, it has been necessary for cell division and replication to additionally supply a "cell growth factor" as a nutrient. Examples of such a cell growth factor include various types of hormones, insulin, putrescine, and a fibroblast growth factor. However, such cell growth factors have not yet been clarified in all cell species, and unknown ingredients are included in many cases.

Hence, instead of cell growth factors, animal serums can be used. The effects thereof can be non-specifically anticipated. Among such animal serums, bovine serum is usually selected because of a large bovine population and also because it can be stably supplied. Especially, fetal bovine serum has been frequently used because it contains only a small amount of toxic protein. In scientific studies, there are cases where a bovine-derived protein may be contained in a test material, although bovine is not an animal species of interest. However, the use of such a bovine-derived protein as a pharmaceutical for a human or other animal species may cause a problem.

The first problem is related to allergy. When a vaccine or a drug that contains bovine serum is parenterally injected into a human, or animals, a first injection may not cause a problem in many cases. However, a second injection or later injections may cause a problem regarding an allergy reaction. This phenomenon can be immunologically explained. That is, an animal only slightly reacts with a high-molecular substance (e.g. a protein having a molecular weight of 10,000 daltons or more) when the substance is exposed to the animal for the first time, and thus the administered substance is decomposed in vivo. However, a memory regarding exposure remains in immune system. Accordingly, when the same substance (antigen) is exposed to the animal for the second time or later, immunocytes that memorize the first exposure directly react with the substance, and as a result, a vital reaction that is stronger than that of the first exposure occurs in a short time. Depending on the types of humans or animals, there may be cases where they may have an unfavorable reaction with an antigen that is exposed from the outside. Such a reaction is typically referred to as an allergy reaction. Such an allergy reaction causes fever or swelling at an injected site, and in the worst case, humans or animals die from dyspnea due to respiratory obstruction, collapse, and the like.

The second problem is related to the contamination of pathogens or bovine serum antibodies contained in bovine serum. A famous example is contamination with Pestivirus, Retrovirus, Mycoplasma, etc. of bovine origin. Recently, prion that is a pathogen of bovine spongiform encephalopathy (BSE) known as mad cow disease has become a possible problem.

As stated above, although the use of bovine serum may occasionally cause troublesome occurrences, such bovine serum has commonly been used for the production of vaccines particularly used for a veterinary field that targets animals over the world.

However, an attempt not to use bovine serum in the cell culture method (a serum free medium (SFM) and a serum free cell culture method) and the production of an experimental vaccine for bovines using such a serum free medium and such a serum free cell culture method have currently been reported (Makoschey et al., Serum-free produced bovine herpesvirus type 1 and bovine parainfluenza type 3 virus vaccines are efficacious and safe. Cytotechnology, 39: 139-145, 2002). However, the publication does not disclose a vaccine used for animals other than bovines. Moreover, vaccines used for dogs are not disclosed at all.

Furthermore, it has been reported that MDCK cells had been cultured in a serum free medium and that influenza viruses had been then replicate. (Kessler et al., Suitability of MDCK cells grown in a serum-free medium for influenza virus production. In Brown et al., ed., Inactivated influenza vaccines prepared in cell culture. Dev. Biol. Stand. Basel, Karger, 1999, vol. 98, pp 13-21: Merten et al., Production of influenza virus in serum-free mammalian cell cultures. In Brown et al., ed., Inactivated influenza vaccines prepared in cell culture. Dev. Biol. Stand. Basel, Karger, 1999, vol. 98, pp 23-37: Voten et al., Generation and characterization of reassortant influenza A viruses propagated in serum-free cultured MDCK-SF1 cells. In Brown et al., ed., Inactivated influenza vaccines prepared in cell culture. Dev. Biol. Stand. Basel, Karger, 1999, vol. 98, pp 77-87: Voeten et al., Characterization of high-grown reassortant influenza A viruses generated in MDCK cells cultured in serum-free medium. Vaccine 17: 1942-1950, 1999: Keiichi Makisumi et al., Cells that can be used in serum free culture and suspension culture and method of producing viruses used for vaccines using such cells; domestic re-publication of PCT international publication for patent application (A1); International Publication WO01/064846; International Publication Date: 2001. Sep. 7). However, media disclosed in these publications comprised unknown ingredients, or although they are serum-free, they comprised animal-derived ingredients.

As a simple cryopreservation method of cells cultured in a serum free medium, a method comprising adding 10% of dimethyl sulfoxide (DMSO) to an MDSS2 medium (AX-CELL Biotechnologies, F-69610 Saint Genis l'Arentiere) that is one type of SFM, and then cryopreserving Vero cells as monkey kidney-derived cells and BHK-21 cells as hamster kidney-derived cells using the produced medium, has been reported. (Merten et al., A simple serum-free freezing medium for serum-free cultured cells. Biologicals, 23: 185-189, 1995.). However, such an MDSS2 medium comprises 0.3% of peptone derived from casein as an animal protein. In addition, it has also been reported that a medium produced by adding 10% of DMSO to a VP-SFM™ medium (serum-free media) can be applied to cryopreservation of cells that has been cultured in a serum free medium. (Price and Evege, Serum-free medium without animal components for virus production. Focus, 19: 67-69, 1997.). However, the composition of the VP-SFM itself remains unknown.

Thus, it has been desired that a medium that contains no ingredients derived from animals, cells cultured in a medium that contains no ingredients derived from animals, safe vaccines and test reagents, and the like, be developed.

DISCLOSURE OF THE INVENTION

One aspect of the present invention relates to a cell strain induced from MDCK cells as dog kidney-derived cells, which can be cultured without ingredients derived from animals. This cell strain may be either a cell strain deposited under accession No. FERM BP-10225, or a cell strain having biological properties equivalent to those of the above cell strain.

In addition, one aspect of the present invention relates to a method of producing a cell strain, which comprises a step of adapting MDCK cells to a medium that does not contain a serum but contains a cell growth factor and a step of culturing the cells in a medium that contains an RPMI 1640 medium and a soybean-derived peptone but does not contain ingredients derived from animals, so as to produce a cell strain that can be cultured without ingredients derived from animals.

Moreover, one aspect of the present invention relates to a method of producing a virus, which comprises a step of infecting a cell strain with a virus and a step of culturing the infected cell strain to replicate the virus. A medium used for the culture of the infected cell strain may be a medium that contains an RPMI 1640 medium and a soybean-derived peptone but does not contain ingredients derived from animals. A suspension culture method may be used for the culture of the infected cell strain. A virus used herein may be one selected from the group consisting of Paramyxoviridae, Orthomyxoviridae, Rhabdoviridae, Flaviviridae, Caliciviridae, Adenoviridae, Herpesviridae, and Parvoviridae. Moreover, the virus used herein may also be one selected from the group consisting of canine distemper virus, measles virus, canine parainfluenza virus, SV5 virus, influenza virus, rabies virus, Japanese encephalitis virus, canine calicivirus, canine adenovirus type 1 and type 2, human adenovirus, canine herpesvirus, and canine parvovirus type 1 and type 2.

Furthermore, one aspect of the present invention relates to a method of producing a diagnostic antigen using a virus produced by the aforementioned method.

Still further, one aspect of the present invention relates to a method of producing a vaccine using a virus produced by the aforementioned method.

Still further, one aspect of the present invention relates to a medium that contains an RPMI 1640 medium and a soybean-derived peptone but does not contain ingredients derived from animals.

Still further, one aspect of the present invention relates to a medium used for cryopreservation of cells, which is produced by adding 10% by weight of dimethyl sulfoxide to the above medium.

Still further, one aspect of the present invention relates to a cryopreservation method, which comprises a step of cryopreserving a cell strain induced from MDCK cells as dog kidney-derived cells, which can be cultured without ingredients derived from animals, using the aforementioned medium used for cryopreservation of cells.

According to one aspect of the present invention, since a cell strain induced from MDCK cells is cultured without ingredients derived from animals, when a virus produced using such a cell strain is used as a vaccine or test reagent, it is possible to provide a safe vaccine or test reagent.

In addition, according to one aspect of the present invention, since a virus can be replicated using a commercially available inexpensive medium, when a virus is produced using such a medium, it is possible to provide an inexpensive vaccine or test reagent.

Moreover, according to one aspect of the present invention, since a medium does not contain ingredients derived from animals, when cells infected with a virus are cultured in the above medium, it is possible to provide a safe vaccine or test reagent.

Furthermore, according to one aspect of the present invention, since cells can be frozen using a medium that does not contain ingredients derived from animals, it is possible to provide a safe vaccine or test reagent.

It is to be noted that the expressions "does not contain ingredients derived from animals" and "without ingredients derived from animals" are used in the present specification to particularly mean that a medium does not contain an animal-derived protein ingredient that can be a cause of allergy. Examples of an ingredient that can be a cause of allergy include an animal-derived serum, a serum albumin as a portion of the above serum, an animal protein such as a cell growth factor, and various types of additives derived from animals (BACTO™ PEPTONE (enzymatic digest of animal protein), Tryptose phosphate broth, etc.).

BEST MODE FOR CARRYING OUT THE INVENTION

In order to develop a safe and effective vaccine that can be used for dogs, an MDCK cell that is a dog kidney cell system having a wider virus infection spectrum is first selected. When a commercially available basal medium that does not contain ingredients derived from animals, such as Eagle's MEM, RPMI 1640 medium, or Leiovitz's L-15 medium, is used, such MDCK cells do not replicate unless bovine serum is added to the medium. Accordingly, MDCK cells are adapted and subcultured serially.

First, MDCK cells are adapted to a serum free medium that contains a cell growth factor. As a cell growth factor, an epidermal growth factor is preferable. A recombinant epidermal growth factor may also be used. Specific examples of such a medium include OPTI-PRO™ SFM medium (cell culture medium, formulated without any components of animal or human origin, for the growth of cell lines) as a product name (Invitrogen; Catalogue No. 12309-019) and OPTI-MEM™ I REDUCED-SERUM MEDIUM (multi-purpose medium as a product name (Invitrogen; Catalogue No. 31985) that is a modified Eagle's MEM, but examples are not limited thereto. Adaptation of MDCK cells is carried out until replication of the cells is stabilized.

After completion of the aforementioned adaptation, the MDCK cells are then adapted to a medium that contains an RPMI 1640 medium and a soybean-derived peptone but does not contain ingredients derived from animals (hereinafter referred to as an "RPMI/SP medium). Such a soybean-derived peptone is a non-animal peptone and acts as a source of protein. The content of such a soybean-derived peptone in the medium is preferably between 250 µg/ml and 3,000 µg/ml, more preferably between 500 µg/ml and 1,000 µg/ml, and particularly preferably approximately 750 µg/ml.

The content of a protein in the medium is preferably 20 µg/ml or less, more preferably 10 µg/ml or less, and particularly preferably 5 µg/ml or less.

An example of the composition of an RPMI/SP medium, which contains 750 µg/ml soybean peptone, is shown below, but examples are not limited thereto.

(Example of RPMI/SP Medium)
- RPMI 1640 medium (GIBCO; Catalogue No. 21870)
- 15 g of a soybean peptone (peptone from soybean, enzymatic digest, Fluka, Catalogue No. 87972) was dissolved in 1,000 ml of sterilized distilled water, and the obtained solution was then filtrated with a 220-nm filter. Thereafter, 5 ml of the resultant was added to 100 ml of the RPMI 1640 medium.
- L-glutamine was added to the RPMI 1640 medium, resulting in a concentration of 300 mg/l (final concentration: 300 µg/ml).
- As antibiotics, potassium penicillin G, streptomycin sulfate, and amphotericin B were added to the RPMI 1640 medium to concentrations of 100 U/ml, 100 µg/ml and 2.5 µg/ml, respectively (The aforementioned concentrations were all the final concentrations).

MDCK cells were subcultured in the OPTI-PRO™ SFM medium (cell culture medium, formulated without any components of animal or human origin, for the growth of cell lines) until the passage number reached 2, and the cells were then subcultured in the OPTI-MEM™ I REDUCED-SERUM MEDIUM (multi-purpose medium) until the passage number reached 33. Thereafter, the cells were subcultured in an RPMI-SP medium until the passage number reached 28. Thus, the cells were favorably adapted to the RPMI-SP medium, so that growth of the cells could be stabilized. The time required for formation of cell sheets and the passage intervals became constant over the past several passages, and the cells were subcultured to quantities that were 4 times the initial quantities at the intervals of 5 to 7 days. This novel cell strain was named as an "MDCK-SP strain." Further, this cell strain was subcultured in an RPMI/SP medium until the passage number reached 45, so that MDCK cells could be completely adapted to the RPMI/SP medium as a serum free medium. Thus, there was established a cell strain, which was induced from MDCK cells as dog kidney-derived cells and could be cultured without ingredients derived from animals. The MDCK-SP cell strain (which were subcultured in an RPMI/SP medium until the passage number reached 45 and were then subcultured in a serum free medium until the total passage number reached 80) was deposited with the National Institute of Advanced Industrial Science and Technology, an Independent Administrative Institution under the Ministry of Economy, Trade and Industry (Higashi 1-1-1, Tsukuba, Ibaraki, Japan) on Dec. 16, 2004 (accession No. FERM P-20329). It was then transferred to an international deposition under accession No. FERM BP-10225 on Feb. 4, 2005.

The MDCK-SP cell strain is infected with a virus that is sensitive to the MDCK cell strain, and the thus infected cell strain is cultured and replicated, so that the virus can be produced. As a medium used for the culture of such virus, a medium that does not contain ingredients derived from animals is preferable, and the aforementioned RPMI/SP medium is more preferable.

Known methods can be used in the culture of the infected cell strain. Examples of such known methods include a monolayer culture method and a suspension culture method.

For example, such a monolayer culture method comprises infecting cells that have been monolayer-cultured in the inner surface of a vessel with a virus of interest and then subjecting the infected cells to a standing culture or a roll-streak culture, so as to prepare the virus in the culture supernatant. As a vessel, a plate culture vessel or a roll-streak culture flask can be used, for example. Specific examples of such a vessel include a Petri dish and a T flask. As a material of such a vessel, a non-glass material is preferable, and a plastic is more preferable.

An example of the suspension culture method is a microcarrier method using microcarrier beads. For example, such a microcarrier method comprises allowing cells to replicate in the form of a monolayer on the surfaces of microcarrier beads in a bioreactor (culture tank), and then infecting the cells replicated on the microcarrier beads with viruses, followed by culturing while stirring, so as to prepare viruses of interest in the culture solution. Examples of materials of such microcarrier beads include ceramic, dextran, glass, silicon, plastic, and polyacrylamide. As commercially available beads, CYTODEX™ (general-purpose microcarrier) manufactured by Amersham Bioscience can be used, for example.

Examples of a virus sensitive to MDCK-SP cells include, but not limited to, Rhabdoviridae, Poxviridae, Picornaviridae, Reoviridae, Adenoviridae, Caliciviridae, Adenoviridae, Paramyxoviridae, Orthomyxoviridae, Flaviviridae, Herpesviridae, and Parvoviridae. Of these, preferred viruses that are able to easily adaption are viruses belonging to Paramyxoviridae, Orthomyxoviridae, Rhabdoviridae, Flaviviridae, Caliciviridae, Adenoviridae, Herpesviridae, and Parvoviridae. Preferred viruses further include canine distemper virus, measles virus, canine parainfluenza virus, SV5 virus, influenza virus, rabies virus, Japanese encephalitis virus, canine calicivirus, canine adenovirus type 1 and type 2, human adenovirus, canine herpesvirus, and canine parvovirus type 1 and type 2. If a technique of acclimatizing viruses to the cultured cells, which is known as "adaptation," were used, the sensitivity spectrum of MDCK-SP cells could be extended.

A virus produced by the method of the present invention is recovered and purified, so that it can be used for a vaccine or a diagnostic antigen substance. For such recovery and purification of a virus, known methods can be used. For example, cells are frozen and then thawed to disrupt them, and the thawed solution is then centrifuged to eliminate cells or disrupted cell debris, so that the supernatant may be recovered as a virus stock.

When a vaccine is produced from the above virus, the produced vaccine may be either an inactivated vaccine or a live vaccine. When an inactivated vaccine is produced, the recovered and purified virus may be inactivated with formalin or the like, and an adjuvant may be added to the thus inactivated virus. On the other hand, when a live vaccine is produced, an attenuated virus may be produced, and it may be then recovered and purified. Thereafter, an adjuvant may be added to the resultant virus. The viral level in a vaccine should be a level sufficient for imparting to a dog to which the vaccine is to be administered, immunity that is necessary for inhibiting infection with the virus as a target. In general, such a viral level is between $1\times10^{3.5}$ $TCID_{50}$/ml and $1\times10^{5.0}$ $TCID_{50}$/ml, or more. An example of the adjuvant used herein is an adjuvant that is able to impart systemic infection protective immunity or local infection protective immunity to a dog to which the vaccine is to be administered.

When a diagnostic agent for infections is produced, the inactivated virus as stated above is used as an antigen, or an antigen isolated from a virus is fixed on a supporting medium such as an ELISA plate or a nitrocellulose membrane, so as to prepare the diagnostic agent. Such a diagnostic agent is allowed to bind to an antibody existing in the serum of a dog. Thereafter, they are allowed to react with a secondary antibody to which horseradish peroxidase or alkaline phosphatase has bound, and it is then subjected to a known reaction such as a color reaction, so that it can be visualized. Thus, the presence or absence of a circulating antibody existing in a dog infected with various types of viruses, namely, the presence or absence of infection, can be detected and confirmed.

When cells are preserved at a low temperature, a medium produced by adding dimethyl sulfoxide (DMSO) to the RPMI/SP medium of the present invention can be used. The amount of DMSO contained in the RPMI/SP medium is preferably between 10% and 20% by weight, and more preferably approximately 10% by weight, based on the weight of the above medium. When cells have been preserved at a low temperature, for example, using an electric freezer at −80° C. or liquid nitrogen at −196° C., a medium containing fetal bovine serum and DMSO has conventionally been used to prevent the cells from physicochemical damage occurred during freezing. In contrast, since the medium of the present invention, which is used in cryopreservation of cells, contains neither serum nor any other ingredients derived from animals, it is suitably used in low-temperature preservation of cells adapted to a serum free medium. In particular, the medium of the present invention is preferable as a medium used in cryopreservation of the MDCK-SP cells.

The invention of the present application will be described more in detail in the following examples. However, these examples are not intended to limit the scope of the present invention. It is to be noted that the term "%" is used in the present specification to mean "% by weight" unless otherwise specified.

Example 1

Production of MDCK-SP Strain Using RPMI/SP Medium

MDCK cells used as dog kidney-derived cells in the present example are related to a cell system produced from the kidney of a healthy female cocker spaniel by Madin & Darby on September 1958. It is considered that this cell system is derived from cells (ATCC No. CCL-34) registered with ATCC (American Type Culture Collection). In 1970, the inventor of the present application used these cells for studies in the Lab. of Veterinary Microbiology, Department of Veterinary Medicine, Faculty of Agricultural, the University of Tokyo. Thereafter, the same above cells were transferred to the Lab. of Veterinary Microbiology, Department of Veterinary Medicine, Faculty of Agricultural, Kagoshima University, and were then transferred to the Lab, of Clinical Microbiology, Kyoritsu Seiyaku Corp. In the Lab. of Clinical Microbiology as the final holder, from April 1995, the cells were subcultured in a medium (7.5% MEM) produced by adding 7.5% fetal bovine serum, 10% tryptose phosphate broth, and L-glutamine (0.292 g/l), and for the purpose of prevention of bug's contamination, also adding penicillin (100 U/ml), streptomycin (100 μg/ml), and amphotericin B (0.25 to 0.5 μg/ml), to an Eagle's MEM basal medium (manufactured by Nissui Pharmaceutical Co., Ltd.; Eagle MEM medium (Nissui (1)). These were defined as parent cells.

As a first step of adaptation, the cells were subcultured in a serum free medium containing a recombinant epidermal growth factor, the product name of which was OPTI-PRO™ SFM (cell culture medium, formulated without any components of animal or human origin, for the growth of cell lines) (Invitrogen; Catalogue No. 12309-019), until the passage number reached 2. Thereafter, the culture solution was exchanged with a modified Eagle's MEM having a product name OPTI-MEM™ I REDUCED-SERUM MEDIUM (multi-purpose medium) (Invitrogen; Catalogue No. 31985). In this medium, the cells were subcultured with no addition of fetal bovine serum, until the passage number reached. Basically, the cells were treated under the same subculture conditions as those of the parent cells. That is to say, the original cells were subcultured to quantities that were 4 times the initial quantities at the intervals of approximately 7 days. In the case of subculturing both the parent cells and MDCK-SP cells induced from the above parent cells and adapted to a serum free medium, the cell surfaces were washed twice with a 0.25% trypsin+0.02% EDTA (ethylenediaminetetraacetic acid) solution, and the cells were then left at rest in an incubator at 37° C., so that the cells were dispersed. The used trypsin was swine pancreas-derived DIFCO™ TRYPSIN 250 (culture media) (Nippon Becton Dickinson Co., Ltd.). The above trypsin was dissolved in sterilized PBS and was then filtrated through a 220-nm filter for sterilization.

As often observed in the process of cell adaptation, cell growth was delayed at times. Thus, during such delay, the medium was exchanged with a fresh medium one or two times, or the expanding factor was reduced to 2 or 3 times, so as not to interrupt the cell growth.

Consequently, a clear effect of subculturing the cells in the OPTI-PRO™ SFM (cell culture medium, formulated without any components of animal or human origin, for the growth of cell lines) and OPTI-MEM™ I REDUCED-SERUM MEDIUM (multi-purpose medium) until the total expanding number reached 35 was obtained. That is, the cell growth was stabilized.

Subsequently, the inventor has attempted to culture the 33$^{rd}$-generation cells, which had been almost adapted to the OPTI-MEM™ I REDUCED-SERUM MEDIUM (multi-purpose medium), in Eagle's MEM, RPMI 1640 Medium, Leiovitz's L-15 Medium, or McCoys 5A Medium. As a result, the cells favorably replicated in the McCoys 5A Medium (modified) (GIBCO Base Catalogue Nos. 12330 and 16600). However, in the case of using other medium, the cell growth terminated on the mid course although they adhered to the wall of the incubation vessel. Thus, a cell sheet was not formed.

A clear difference obtained by a comparison made between the ingredients of the McCoys 5A Medium (modified) (GIBCO Base Catalogue Nos. 12330 and 16600) and those of other basal media was addition or non-addition of BACTO™ PEPTONE (enzymatic digest of animal protein). Such BACTO™ PEPTONE (enzymatic digest of animal protein) was a "nutrient" obtained by digestion of various types of bovine proteins with enzymes. Thus, since BACTO™ PEPTONE (enzymatic digest of animal protein) was not matched with the intention of the present invention, the McCoys 5A Medium was used as a comparison example. It is considered that the cells favorably replicated in the McCoys 5A Medium because of the influence of BACTO™ PEPTONE (enzymatic digest of animal protein) as a bovine protein-derived enzyme digest, which had been added only to the McCoys 5A Medium. Thus, various types of non-animal peptones acting also as protein sources were examined. As a result, the inventor has found a soybean-derived peptone.

Among the aforementioned basal medium, namely, Eagle's MEM, RPMI 1640 Medium, and Leiovitz's L-15 Medium, cell growth in RPMI 1640 Medium was the most excellent. Thus, such RPMI 1640 Medium was adopted, and a soybean peptone was added to the medium, so as to produce a medium that did not contain an animal-derived protein (referred to as an "RPMI/SP medium). Such an RPMI/SP medium is shown in Table 1. The medium and additives as shown in the table are provided as examples, and examples of commercially available products are shown herein. Accordingly, the RPMI/SP medium of the present invention is not limited thereto.

[Table 1]

TABLE 1

A specific example of RPMI/SP medium

1) RPMI 1640 Medium (GIBCO, Catalogue No. 21870)
2) 15 g of soybean peptone (peptone from soybean, enzymatic digest, Fluka, Catalogue No. 87972) was dissolved in 1,000 ml of sterilized distilled water, and the obtained solution was then filtrated through a 220-nm filter. Thereafter, 5 ml of the filtrate was added to 100 ml of the medium of 1) (final concentration: 750 µg/ml).
3) L-glutamine was added to the above mixture to a concentration of 300 mg/l (final concentration: 300 µg/ml).
4) As antibiotics, potassium penicillin G, streptomycin sulfate, and amphotericin B were added to the obtained mixture to concentrations of 100 U/ml, 100 µg/ml and 2.5 µg/ml, respectively. (The aforementioned concentrations were all the final concentrations.)

The culture vessel used for culture was a non-glass vessel, for example, a plastic vessel such as a 25-cm$^2$ T flask or a plastic Petri dish with a diameter of 6 cm. Using such a culture vessel, culture was initiated in a serum free culture. As a result, the original wall adhesive property of MDCK cells was attenuated. The cells adhered to the glass wall, but extension and replication of the cells were not observed. Thus, the cells formed neither a cell mass nor a cell sheet. Accordingly, a plastic culture vessel was used in all the processes of the present invention.

MDCK cells, which had been subcultured in the OPTI-PRO™ SFM (cell culture medium, formulated without any components of animal or human origin, for the growth of cell lines) and OPTI-MEM™ I REDUCED-SERUM MEDIUM (multi-purpose medium) until the total passage number had reached 35, were then adapted to and subcultured in the medium as shown in Table 1. When the above cells were subcultured in the RPMI/SP medium until the passage number reached 28, it was confirmed that the cells were clearly adapted to the above medium, and that the cell growth could be stabilized. That is to say, the time required for formation of cell sheets and the passage intervals became constant over the past several passages, and the cells were subcultured to quantities that were 4 times the initial quantities at the intervals of 5 to 7 days. The cells were further subcultured, and when the passage number reached 45, the cells could be completely adapted to the RPMI/SP medium as a serum free medium. Thus, the 45$^{th}$-generation cell strain was defined as a newly induced cell strain, and it was deposited with the aforementioned international institutions, as stated above (MDCK-SP strain).

Figure 1:
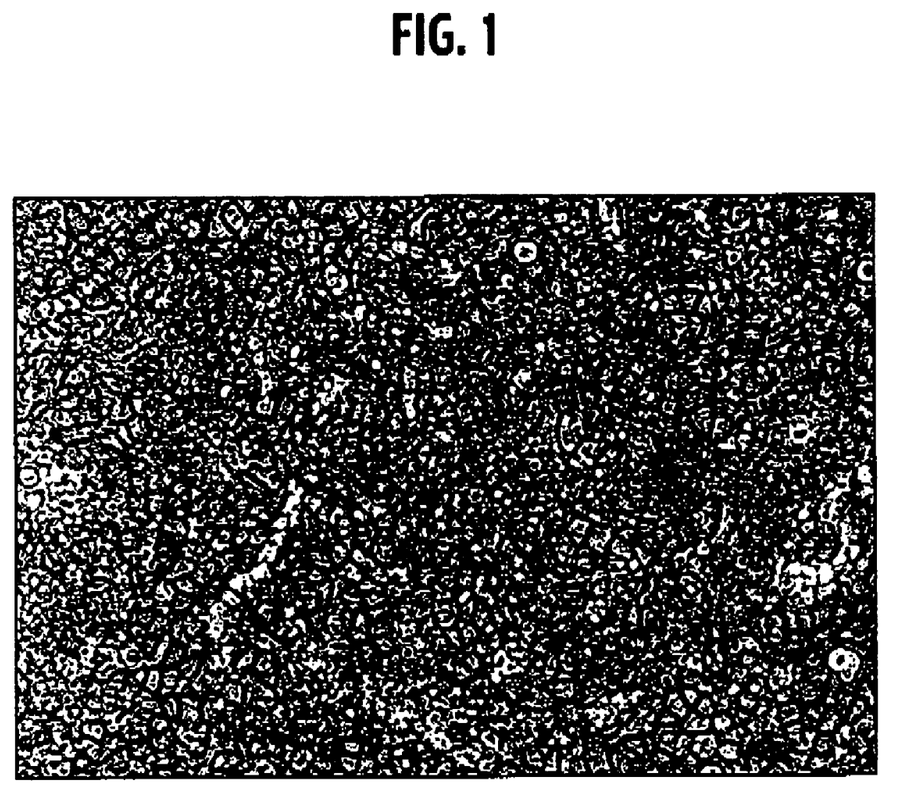
FIG. 1 is a photograph showing the cells of an MDCK-SP strain.

FIG. 1 shows a photograph of a cell sheet taken on the 3$^{rd}$ day of the culture of the 40$^{th}$-generation MDCK-SP cell strain. The photograph was taken under an inverted microscope, while the cells were neither immobilized nor stained. Thereafter, the number of the cells further increased, and the sheet thereby became thickened.

Figure 2:
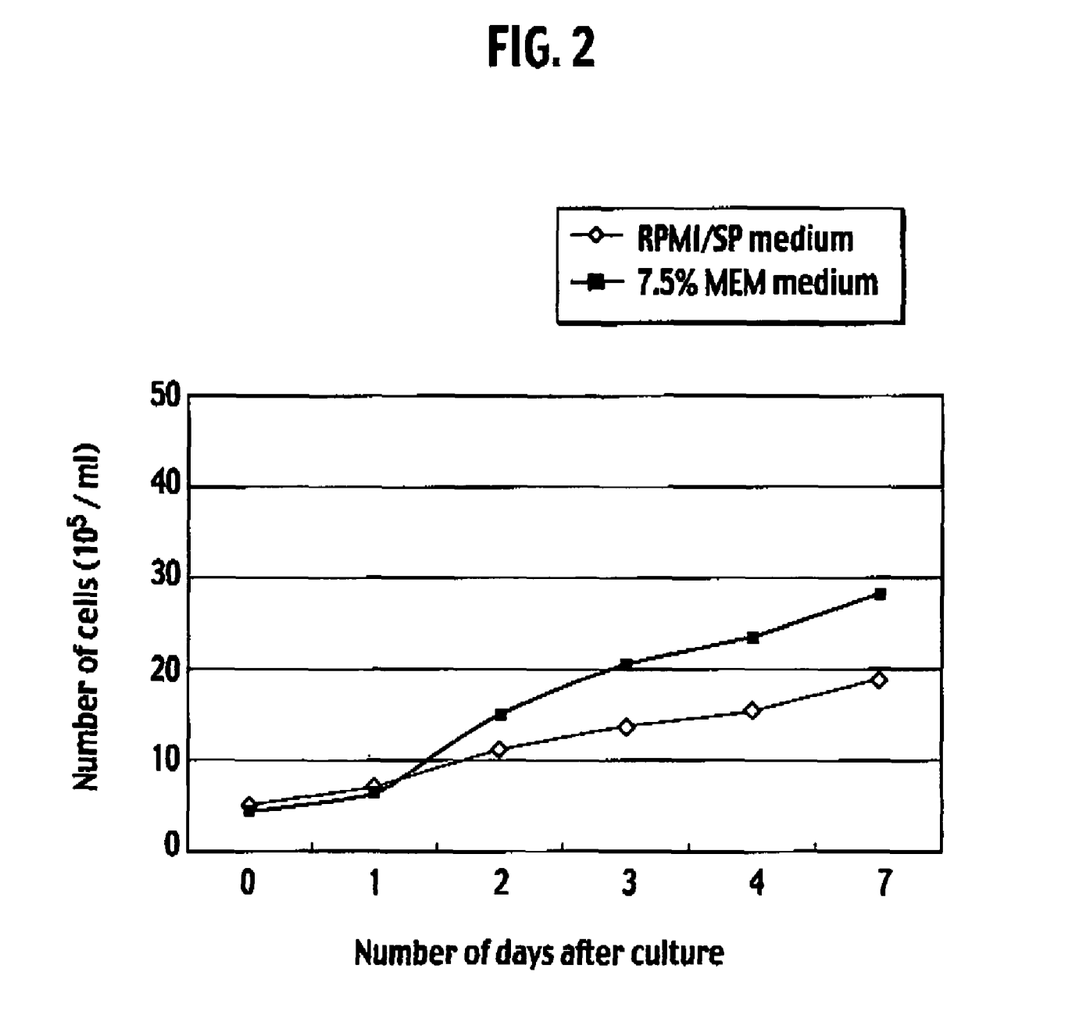
FIG. 2 is a view showing growth curves of MDCK-SP cells cultured in an RPMI/SP medium and MDCK cells cultured in 7.5% MEM.

FIG. 2 shows the growth curb of the 41$^{st}$-generation MDCK-SP cells cultured in the RPMI/SP medium. Culture of parent cells used as controls were initiated in 7.5% MEM. In the case of both types of cells, 7.5 ml of the cell suspension having a cell concentration that had been controlled to $5.0 \times 10^5$/ml was placed in a 25-cm$^2$ T flask, and it was then subjected to a standing culture in a closed system. The number of cells was counted every 24 hours. As shown in FIG. 2, seven days later, the quantities of the MDCK-SP cells increased to approximately 4 times the original quantities thereof, and the quantities of the parent cells increased to approximately 5.5 times the original quantities thereof. From such results, it is found that the MDCK-SP cells were excellent in terms of replication, as well as the MDCK cells as parent cells.

Other than the aforementioned property, the MDCK-SP cells had the following properties.

An attempt was made to culture the 44$^{th}$-generation MDCK-SP cells in an RPMI 1640 Medium, to which no soybean peptones had been added. Four days later, the initial generation formed a cell sheet. However, after the cells had been subcultured, they replicated only in a nest form and did not form a cell sheet. From such results, it was reconfirmed that the induced MDCK-SP cell strain needs a soybean peptone contained in the RPMI/SP medium for its replication.

With regard to the influence of the MDCK-SP cells on replication when the amount of soybean peptones contained in the RPMI/SP medium was changed to 2 times and 4 times, namely, to 1.5 mg/ml and 3 mg/ml, the MDCK-SP cells from 47$^{th}$ generation were examined. As a result, it was found that the MDCK-SP cells replicated at the same level although the amount of a soybean peptone was increased.

Example 2

Suspension Culture of Cells Using Microcarrier Beads

The MDCK-SP cells were subjected to a suspension culture using commercially available microcarrier beads.

CYTODEX™ (general-purpose microcarrier) of Amersham Bioscience was used as commercially available microcarrier beads. This is a sphere consisting of dextran, which is specifically used in cell culture.

0.3 g of microcarrier beads was weighed, and it was then activated with a phosphate buffered saline that did not contain $Ca^{++}$ and $Mg^{++}$ in accordance to the instructions. Thereafter, it was sterilized by heating with an autoclave, followed by substitution with an RPMI/SP medium. This suspension of microcarrier beads was transferred into a spinner flask (Wheaton Science Products, NJ, USA). The total $10^7$ MDCK-SP cells (the $56^{th}$-generation) were then suspended in 50 ml of RPMI/SP medium, and the suspension was then placed in the flask, so that the cells were adsorbed at 37° C. For approximately 3 hours, the suspension was occasionally rotated at 40 rpm for about 2 minutes, so that the cells were mixed with and allowed to come into contact with the sphere. Thereafter, 50 ml of RPMI/SP medium was further added to the suspension, and while the total 100 ml of the mixture was rotated in the spinner at 60 rpm, the culture was initiated.

Figure 3:
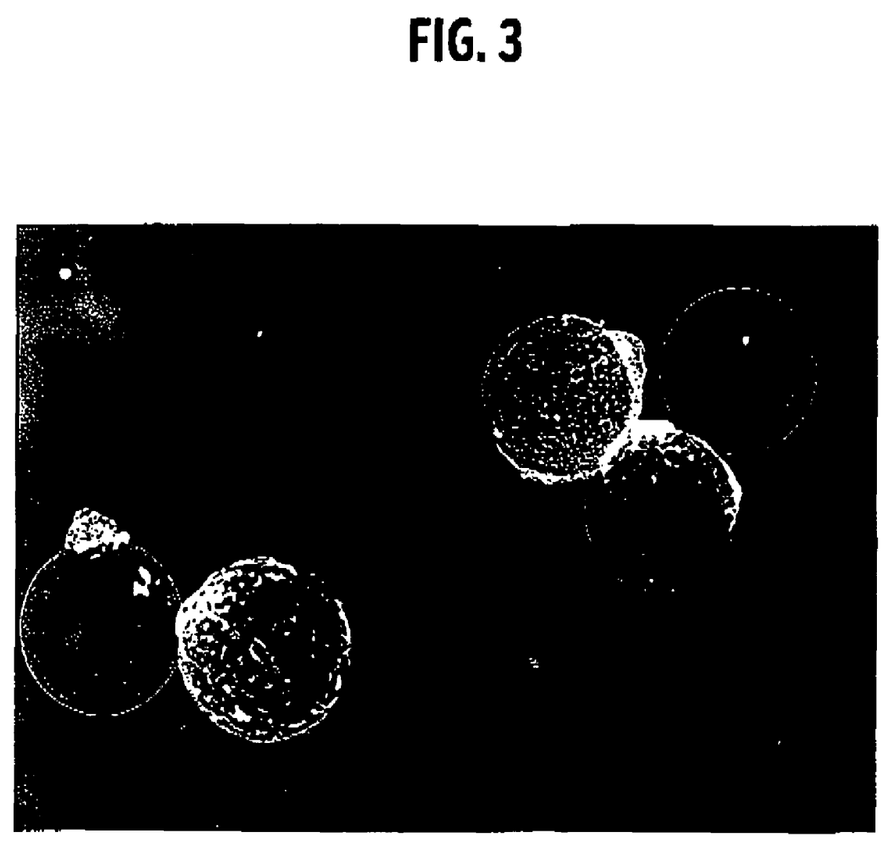
FIG. 3 is a photograph showing MDCK-SP cells that have been subjected to a cell suspension culture using an RPMI/SP medium and microcarrier beads.

After initiation of the culture, a half of the medium was exchanged with a fresh medium at the intervals of 3 days. 20 days after initiation of the culture, it was observed that several cells were adsorbed on a part of the sphere, and that the color of the medium was changed to yellow, which suggested cell growth. Four days after observation of the above cell adhesion, it was confirmed that the number of the adhered cells increased. FIG. 3 is a photomicrograph taken 27 days after the initiation of the culture.

From FIG. 3, it is found that the sphere surface was covered with the cells. It was possible to recover such adhered cells with the aforementioned trypsin/EDTA solution and to subculture them in new microcarrier beads and medium. That is, the combination of the MDCK-SP cells with the RPMI/SP medium enables a suspension culture of cells using microcarrier beads.

The suspension culture method using microcarrier beads is a technique used for increasing the number of cells generated per unit volume. By this culture method, a canine parvovirus may be replicated using the MDCK/SP cells. This culture method is extremely useful for generation of a virus whose replication level depends on the replicating ability of host cells to be infected with the virus, such as a canine parvovirus. It is anticipated that the level of viruses generated will be significantly increased. For example, since the level of canine parvoviruses contained in 1 vial (1 ml volume) of vaccine for dogs, which is currently commercially available, is between $10^{5.0}$ and $10^{7.0}$ $TCID_{50}$, the purpose can be sufficiently achieved even by a culture method involving the infectivity titers of seed virus stocks as shown in Table 2 below. The suspension culture method using microcarrier beads is applied to solve such a problem specific for cell function-dependent viruses.

Example 3

Production of Serum Free Seed Virus Stock

In Example 3, there were used 5 types of viruses, which currently constitute core vaccines used in preventive inoculation to pet dogs widely over the world, such as canine distemper virus, canine adenovirus type 1 and type 2, canine parainfluenza virus, and canine parvovirus type 2. To date, such virus stocks have been replicated in a cell culture system such as Eagle's MEM that fetal bovine serum or tryptose phosphate broth had been added. Thus, in order to replicate viruses in a serum free medium as a cell culture system, animal proteins such as a bovine serum ingredient should be eliminated. Hence, a serum free seed virus stock was produced in the present example. Table 2 shows the actually used virus strain names, among the aforementioned virus species, and the virus titers of seed virus stocks produced using such virus strains.

[Table 2]

TABLE 2

Viruses of seed virus stocks and infectivity titers

| Virus | Strain name | Cell species | Infectivity titer ($TCID_{50}/0.1$ ml) | |
|---|---|---|---|---|
| | | | 7.5% MEM medium | RPMI/SP medium |
| Canine distemper virus | Snyder-Hill | MDCK | $10^{4.7}$ | $10^{5.5}$ |
| Canine adenovirus type 1 | PR109 | MDCK | $10^{8.5}$ | $10^9$ |
| Canine adenovirus type 2 | Manhattan | MDCK | $10^{6.7}$ | $10^{5.3}$ |
| Canine parvovirus type 2 | MD97-037 | MDCK | $10^{5.5}$ | $10^{4.5}$ |
| Canine parainfluenza virus | Tsukuba | MDCK | $10^{7.7}$ | $10^{8.3}$ |

With regard to the initial virus stocks of canine distemper virus, canine adenovirus type 1 and type 2, and canine parainfluenza virus, after inoculation of the viruses, MDCK cells as parent cells were cultured in a medium, to which 2% fetal bovine serum had been added, so as to promote replication of the viruses. Thus, since 2% bovine serum and 10% tryptose phosphate both are contained in the culture supernatant, the following attempt was made to eliminate the influence of such ingredients. A virus stock was inoculated into MDCK-SP cells, which had been cultured in a closed system flask and had formed a cell sheet, and viruses were then adsorbed thereon for 1 hour. Thereafter, the virus stock was eliminated by aspiration, and the cell surfaces were then washed twice with an RPMI/SP medium. Thereafter, an RPMI/SP medium was added thereto, and the obtained mixture was then subjected to a standing culture in an incubator at 37° C., so as to promote replication of viruses. A few to 7 days later, when viruses sufficiently replicated, the flask that contained the culture was once frozen and then thawed. The thawed solution was subjected to a low-speed centrifugation to remove cells and cell-debris. The supernatant was defined as a $2^{nd}$-generation virus stock. This operation was repeated two times in total, and the obtained $3^{rd}$-generation culture supernatant was defined as a virus stock, and it was poured in a freezer of −80° C. and was preserved.

With regard to canine parvovirus type 2, the virus was inoculated into the MDCK-SP cells, when the cells were suspended in an RPMI/SP medium. The initial virus stock contained 7.5% fetal bovine serum, and thus the influence of the bovine serum in the initial virus stock was greater than that in other virus stocks. Hence, when the MDCK-SP cells were suspended in the RPMI/SP medium, a virus stock in an amount of approximately 5% of the culture solution was added to the suspension, and the mixed solution was then subjected to a standing culture in an incubator at 37° C. Twenty-four hours after adhesion of the cells to the wall, the culture solution was eliminated by aspiration, and the cell surfaces were washed once with an RPMI/SP medium. Thereafter, a new RPMI/SP medium was added to the incubator to promote replication of the virus. Further 6 days later, the infected cells themselves were subcultured in the same subculture operation as the subculture of normal MDCK-SP cells by digestion with trypsin. This operation was repeated twice in total, and the 3$^{rd}$-generation culture contained in a flask was once frozen and thawed. The thawed solution was subjected to a low-speed centrifugation to eliminate cells and cell debris. The supernatant was defined as a seed virus stock.

The infectivity titers of virus species produced in the MDCK-SP cells cultured in the RPMI/SP medium are also shown in Table 2. From Table 2, it was found that such infectivity titers are equivalent to there of the virus replicated in MDCK cells as parent cells.

Example 4

Growth of Canine Distemper Virus

1) MDCK cells used as parent cells were cultured in a 7.5% MEM medium placed in a 25-cm$^2$ T flask. MDCK-SP cells were cultured in an RPMI/SP medium placed in the same type of flask. Three days after initiation of the culture, a sheet was formed. At that time, the number of cells was counted.

2) A canine distemper virus, Snyder Hill strain, from among the virus stocks as shown in Table 2, was diluted and then inoculated into the two above types of cells, such that the two types of cells could have the same m.o.i. (multiplicity of infection; the ratio of the number of infective viral particles and a known number of cultured cells), which was 0.01.

3) After the viruses had been adsorbed at 37° C. for 1 hour, unadsorbed viruses were eliminated by aspiration. Thereafter, 7.5% MEM or an RPMI/SP medium was added to the flask, followed by a standing culture.

4) Subsequently, after inoculation at the intervals of 24 hours, the culture contained in the flask was cryopreserved in a freezer of −80° C. at the 1$^{st}$, 2$^{nd}$, 3$^{rd}$, 4$^{th}$, and 7$^{th}$ days.

5) Before the measurement of virus infectivity titers, the frozen flask was thawed at a room temperature, and a supernatant obtained by eliminating cell components by centrifugation at 2,500 rpm for 10 minutes was then used in the measurement of an infectivity titer.

6) Such an infectivity titer was measured by a micro-titration method using a 96-well microplate. That is to say, the virus stock obtained in 5) above was diluted 10 times with 7.5% MEM medium by a serial dilution, and 100 µl of each dilute was added to 4 wells. Thereafter, 100 µl of a cell suspension was further added to all wells, and the obtained mixture was lightly blended, followed by a standing culture in a 5% carbon dioxide incubator at 37° C.

7) As such a cell suspension, Vero cells (SLAM Vero), which expressed canine SLAM (CD150) as a cell side receptor for canine distemper virus to a concentration of 1×10$^5$/ml in 7.5% MEM, were used. (Seki et al., Efficient isolation of wild strains of canine distemper virus in Vero cells expressing canine SLAM (CD150) and their adaptability to marmoset B95a cells. J. Virol., 77: 9943-9950, 2003).

8) Seven days after virus inoculation, the end point of an infectivity titer was calculated based on the presence or absence of cytopathic effect (CPE).

Figure 4:
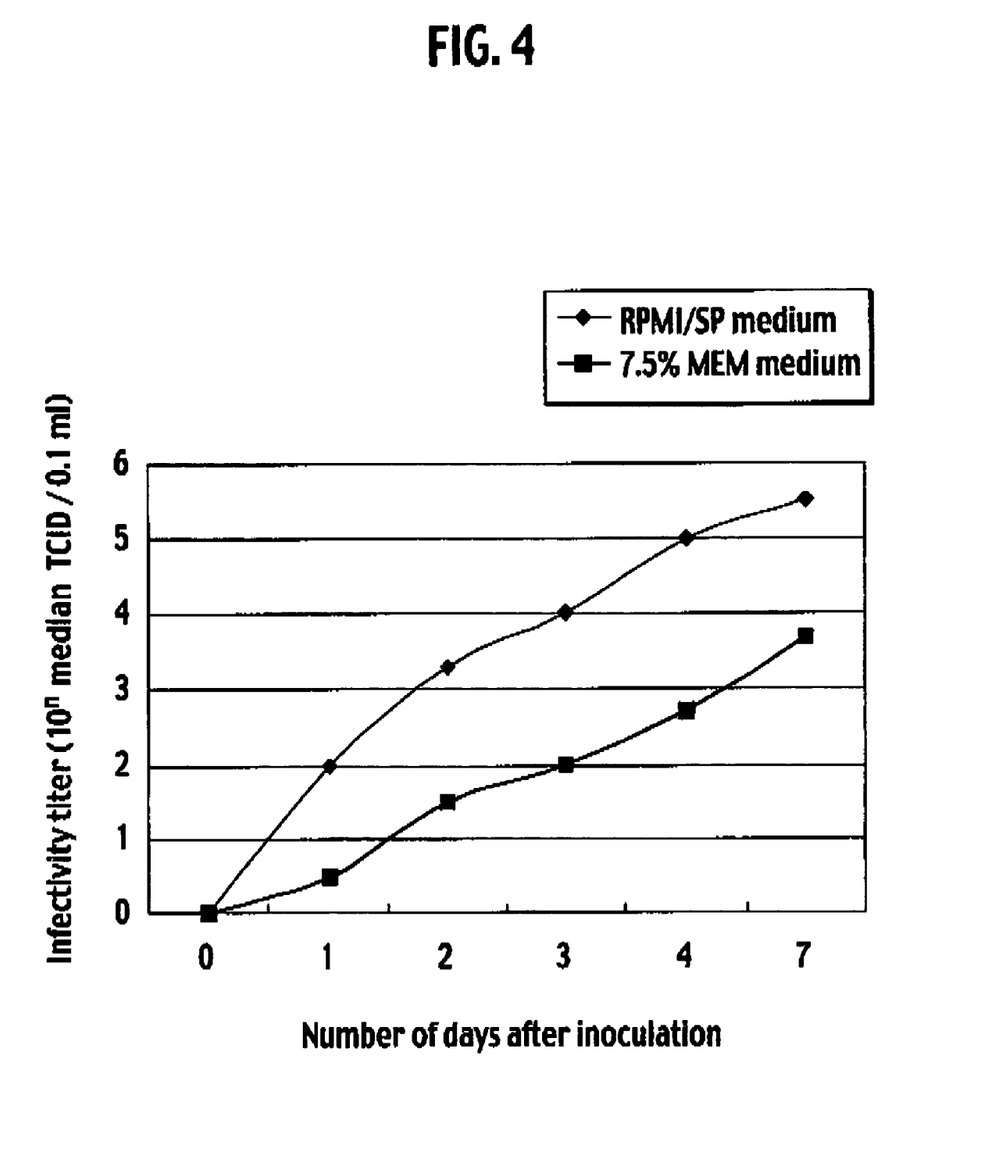
FIG. 4 is a view showing growth curves of canine distemper virus Snyder Hill strains in MDCK cells cultured in 7.5% MEM and in MDCK-SP cells cultured in an RPMI/SP medium.

The results are shown in FIG. 4. FIG. 4 shows growth curves of the canine distemper virus Snyder Hill strains in MDCK cells as parent cells cultured in 7.5% MEM and in MDCK-SP cells cultured in the medium of the present invention that contained no proteins derived from animals. From the day after virus inoculation, in both the parent MDCK cells and the MDCK-SP cells, the virus was started to be generated at 24 hours after infection, and the number of the viruses then increased. At all time points, the MDCK-SP cells exhibited virus infectivity titers that were 32 to 100 times higher than those of the MDCK cells.

Example 5

Canine Adenovirus Type 1 and Type 2

The same method as that described in Example 4 was applied herein with the following two exceptions:

1) The used virus strains were a PR109 strain in the case of canine adenovirus type 1 (CAV-1) and a Manhattan strain in the case of canine adenovirus type 2 (CAV-2); and 8) The cells used in the micro-titration method for the infectivity titration were the MDCK cells.

Figure 5:
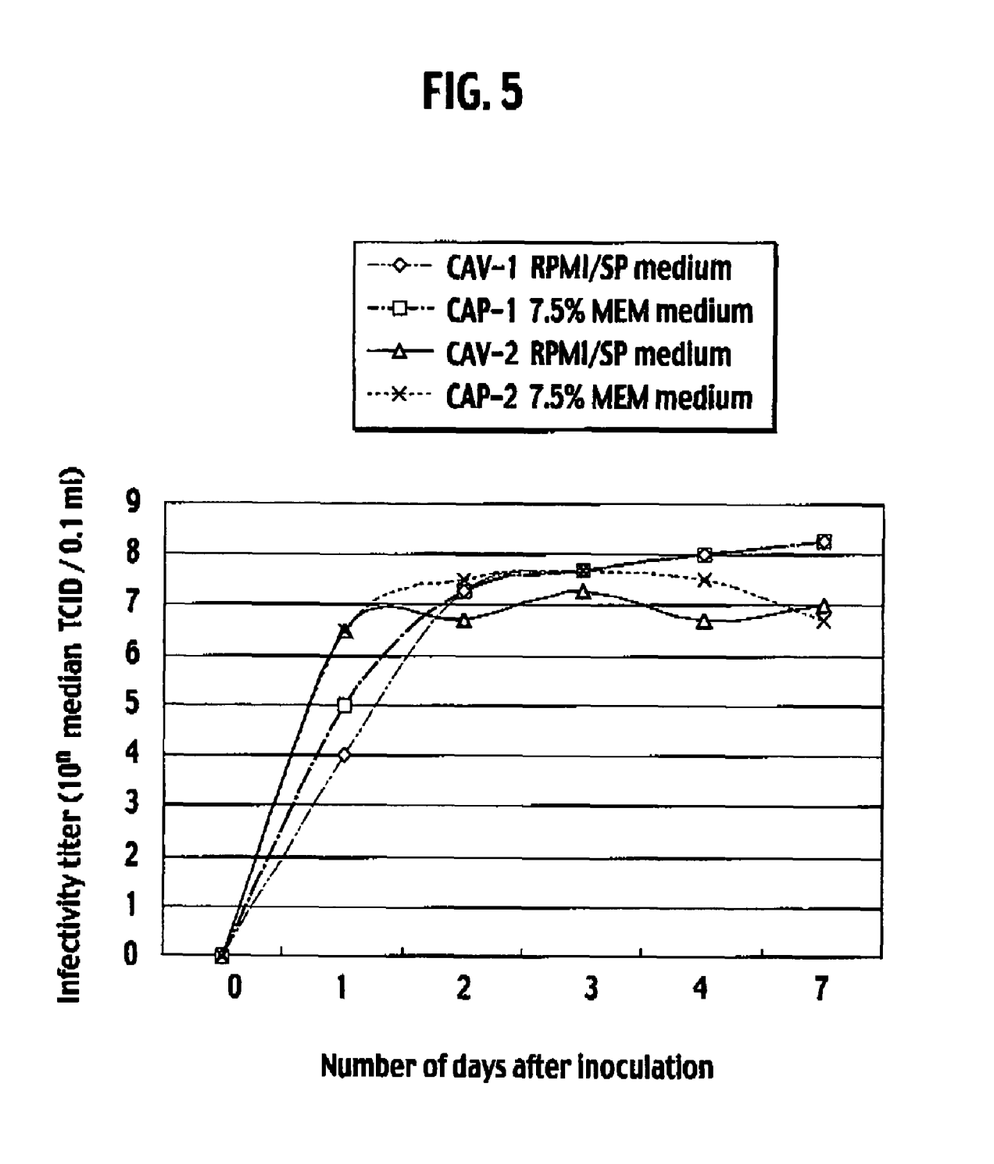
FIG. 5 is a view showing growth curves of canine adenovirus type 1 RP109 and type 2 Manhattan strains in MDCK cells cultured in 7.5% MEM and in MDCK-SP cells cultured in an RPMI/SP medium.

The results are shown in FIG. 5. From FIG. 5, it is found that the two types of virus stains replicated in almost the same manner in the two types of cultured cells. In addition, there was no difference between the conventional virus culture method using bovine serum and the virus culture method of the present invention using MDCK-SP cells cultured in a medium that contained no proteins derived from animals. In the two above types of methods, excellent infectivity titers were obtained.

Example 6

Canine Parainfluenza Virus

The same method as that described in Example 4 was applied herein with the following three exceptions:

1) The used virus strain was a Tsukuba strain;

2) The cells used in the micro-titration method for the measurement of infectivity titers were the MDCK cells; and 3) According to the presence or absence of a hemagglutinin generated in a supernatant contained in each dilution well, an infectivity titer end point used in the micro-titration method for the measurement of infectivity titers was determined. That is, 50 µl of the supernatant was collected from each well, and it was then transferred to a microplate that had been separately prepared for a hemagglutination reaction. Thereafter, to each of all the wells, an equal amount of phosphate buffered saline (PBS; pH 7.0) and an equal amount of rhesus blood cell suspension were added. Such a rhesus blood cell suspension was prepared by suspending 0.75% blood erythrocytes in the same type of PBS. The obtained mixture was fully stirred, and it was then left at rest at a room temperature for 2 hours. Thereafter, the infectivity titer was calculated based on the presence or absence of hem agglutination.

Figure 6:
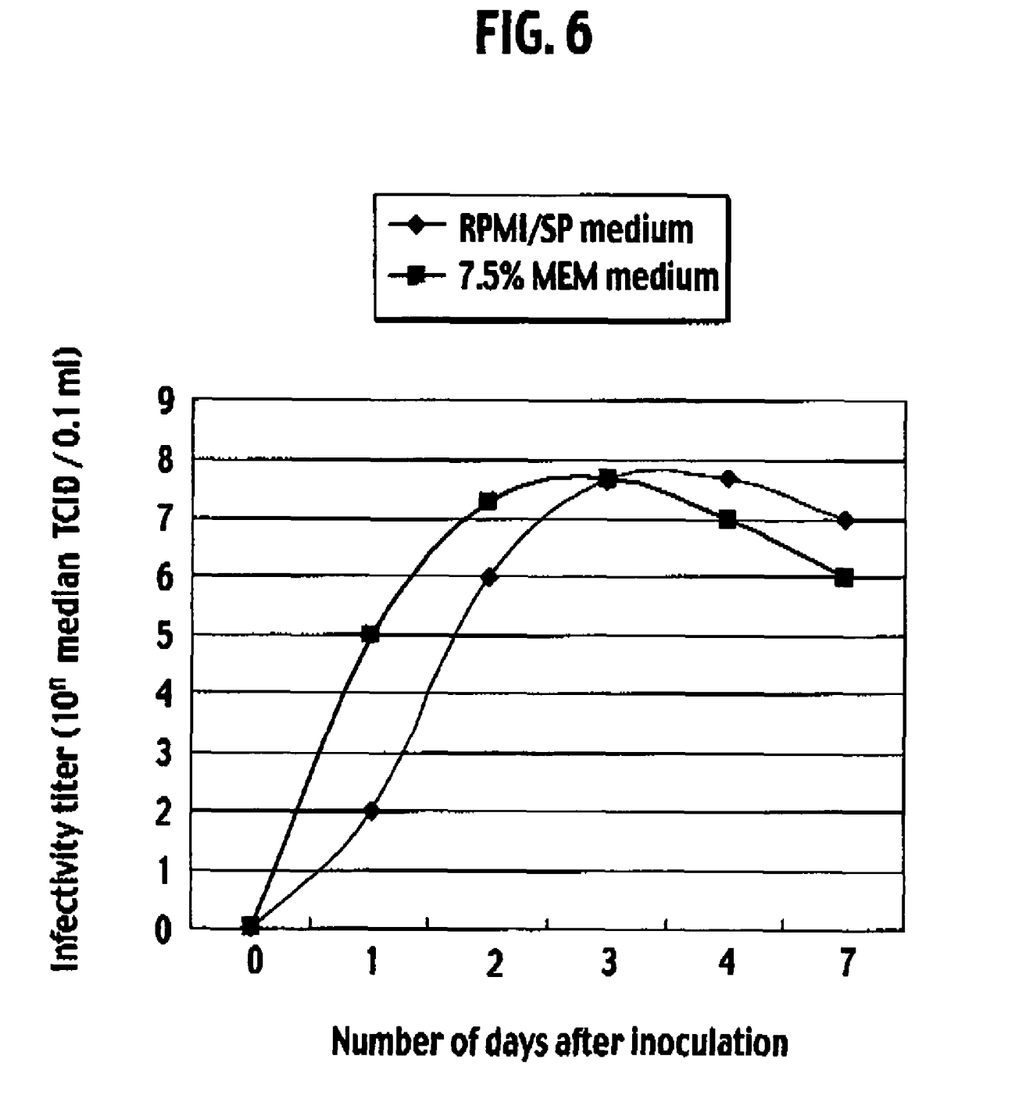
FIG. 6 is a view showing growth curves of canine parainfluenza virus Tsukuba strains in MDCK cells cultured in 7.5% MEM and in MDCK-SP cells cultured in an RPMI/SP medium.

The results are shown in FIG. 6. According to FIG. 6, the time required for reaching the peak of virus replication in the conventional virus culture method using bovine serum was approximately 24 hours faster than that in the method of the present invention using MDCK-SP cells cultured in a medium that contained no proteins derived from animals. However, there was no difference in terms of the reached virus titers between the conventional maximum virus culture method using bovine serum and the method of the present invention using MDCK-SP cells cultured in a medium that contained no proteins derived from animals.

Example 7

Canine Parvovirus Type 2

The same method as that described in Example 4 was applied herein with the following five exceptions:

1) The used virus strain was an antigenic type 2b MD 97-037 strain;
2) A virus stock was diluted, so as to be m.o.i. of 0.05, and the virus was inoculated when the cells were suspended in the medium, as described in Example 3;
3) The cells used in the micro-titration method for the measurement of infectivity titers were the MDCK cells;
4) According to the presence or absence of a hemagglutinin generated in a supernatant contained in each dilution well, an infectivity titer end point was determined, as described in Example 6; and
5) The pH of PBS used in the operation was pH 6.8, and the reaction was carried out at 4° C.

Figure 7:
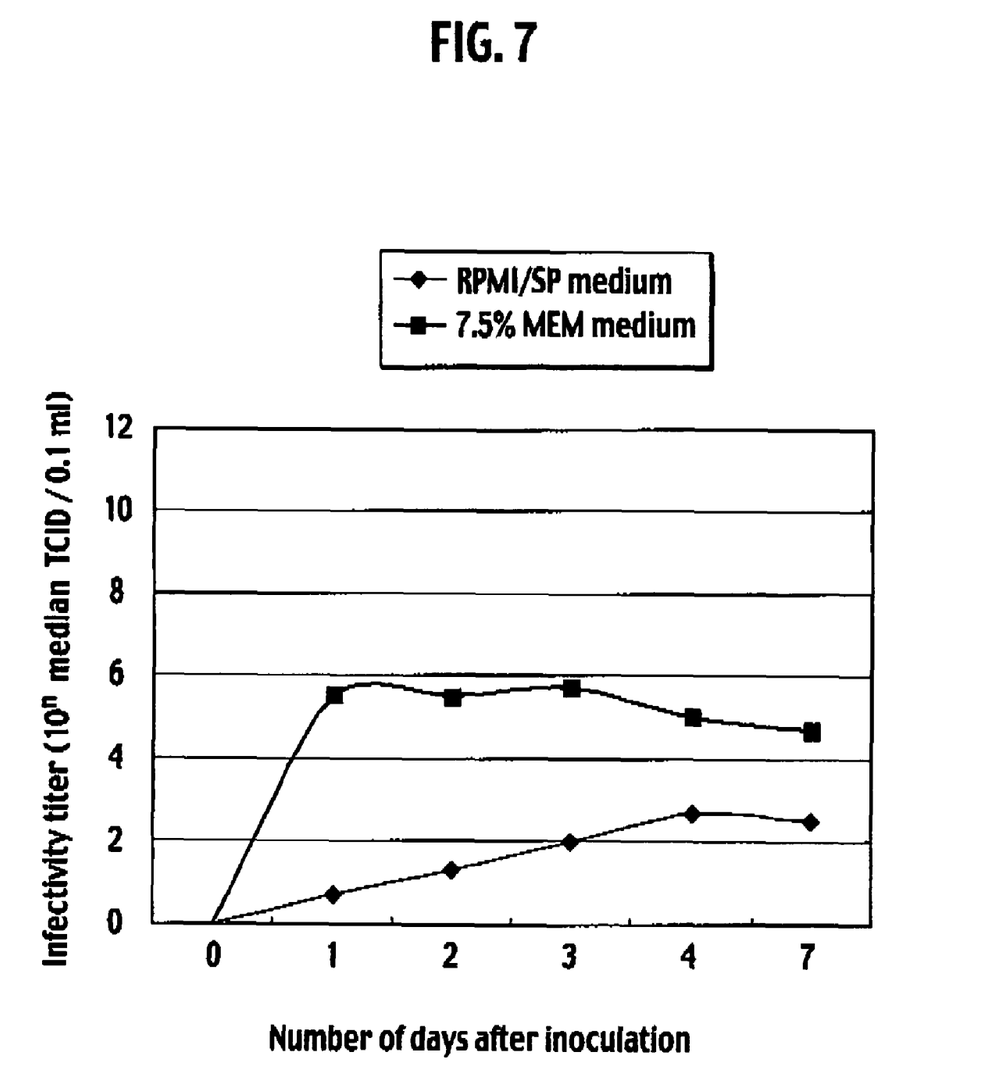
FIG. 7 is a view showing growth curves of canine parvovirus type 2, antigenic type 2b MD 97-037 strains in MDCK cells cultured in 7.5% MEM and in MDCK-SP cells cultured in an RPMI/SP medium.

The results are shown in FIG. 7. Differing from the virus species of Examples 4 to 7, the conventional virus culture method using bovine serum brought on a higher level of virus than that by the virus culture method using MDCK-SP cells cultured in a medium that contained no proteins derived from animals. According to FIG. 7, however, a virus culture method using MDCK-SP cells cultured in a medium that contained no proteins derived from animals also exhibited virus infectivity titers sufficient for the practical use.

Parvovirus has generally been known that when host cells actively divide and grow, the level of virus generated also increase. This is because parvovirus does not have a nucleic acid synthetase necessary for replication of viral DNA, and because the above virus uses the DNA polymerase of the host cells infected therewith. In the case of parvovirus, when host cells actively divide and grow, the amount of DNA polymerase also increases, and replication is thereby promoted. In the method of digesting and dispersing virus-infected cells with trypsin and then subculturing the cells in a new medium, as conducted in Example 3, the ratio of virus-infected cells increases in every passage. Thus, by such subculture of the cells, host cells also divide, and the environment is preferably changed to more efficient virus replication. As a result, it is considered that a higher level of virus is generated in a certain amount of medium. On the other hand, as with the present example, in a case where cell growth has a certain limit in an incubator (namely, an area to which the cells adhere and grow is limited) after the cells have been allowed to come into contact with the virus and have been infected therewith, it is considered that virus generation is directly limited, depending on the growth rate or density of the host cells. In order to enhance cell replicating ability (infectivity titer), a virus growth method may be modified by altering cell density, the level of infecting virus, the passage of virus-infected cells, etc.

Example 8

Simple Cryopreservation Method of Cells Cultured in Serum Free Medium

A medium used in cell freezing was prepared by adding 10% DMSO (Wako Pure Chemical Industries, Ltd.; Catalogue No. 043-07216) to an RPMI/SP medium. MDCK-SP cells, which had been subcultured in an RPMI/SP medium until the passage number had reached 44, were suspended in the prepared medium, resulting in a concentration of $10^6$/ml or greater. Then, 1.8 ml each of the suspension was dispensed in a cryopreserving vial. The exact number of cells was found to be $6.5 \times 10^6$/vial. This vial was placed in a simple cell freezer, a BICELL™ (bio-freezing vessel) (Nihon Freezer Co., Ltd.), that had been chilled, and it was then frozen with a freezer of −80° C. overnight. Thereafter, the frozen cells were transferred to liquid nitrogen (liquid phase).

48 hours later, in order to confirm a state of cryopreservation, the frozen cells were removed from the liquid nitrogen according to usual methods, and the cells were then immediately thawed in warm water of approximately 40° C. Thereafter, the thawed cells were diluted and suspended in 10 ml of RPMI/SP medium, and the cells were then recovered by a low-speed centrifugation. A cell pellet was resuspended in 7.5 ml of RPMI/SP medium, and the suspension was then placed in a 25-cm² T flask. The culture was initiated at 37° C.

On day 3 of culturing, a cell sheet was formed. On day 5, the cells were subcultured in a new medium having a volume 4 times the volume of the previous medium. Three days after the subculture, the thus subcultured cells also formed a cell sheet. No adverse effects of this freezing method were found, as far as the cells were observed at least under a microscope. Then, subculturing could be carried out as in the case of non-frozen cells. From such results, it was confirmed that a 10% DMSO-added RPMI/SP medium could be effectively used in freezing the MDCK-SP cells of the present invention.

It is further understood by those skilled in the art that the foregoing description is preferred embodiments of the invention and that various changes and modifications may be made in the invention without departing from the sprit and scope thereof.

The invention claimed is:

1. An isolated cell strain comprising:
    a cell strain deposited under accession No. FERM BP-10225.

2. A method of producing a virus, which comprises:
    infecting the cell strain according to claim 1 with a virus; and culturing the infected cell strain to replicated the virus.

3. The method of producing a virus according to claim 2, wherein a medium used for the culture of the infected cell strain comprises an RPMI 1640 medium and a soybean-derived peptone but does not comprise ingredients derived from animals.

4. The method of producing a virus according to claim 2, wherein culturing the infected cell strain in performed by a suspension culture method.

5. The method of producing a virus according to claim 2, wherein the virus is selected from the group consisting of Paramyxoviridae, Orthomyxoviridae, Rhabdoviridae, Flaviviridae, Caliciviridae, Adenoviridae, Herpesviridae, and Parvoviridae.

6. The method of producing a virus according to claim 2, wherein the virus is selected from the group consisting of canine distemper virus, measles virus, canine parainfluenza virus, SV5 virus, influenza virus, rabies virus, Japanese encephalitis virus, canine calicivirus, canine adenovirus type 1 and type 2, human adenovirus, canine herpesvirus, and canine parvovirus type 1 and type 2.

* * * * *